(12) United States Patent
Oleson, Jr. et al.

(10) Patent No.: US 6,468,967 B1
(45) Date of Patent: Oct. 22, 2002

(54) METHODS FOR ADMINISTRATION OF ANTIBIOTICS

(75) Inventors: Frederick B. Oleson, Jr., Concord; Francis P. Tally, Lincoln, both of MA (US)

(73) Assignee: Cubist Pharmaceuticals, Incorporated, Lexington, MA (US)

( * ) Notice: Subject to any disclaimer, the term of this patent is extended or adjusted under 35 U.S.C. 154(b) by 0 days.

(21) Appl. No.: 09/406,568

(22) Filed: Sep. 24, 1999

Related U.S. Application Data

(60) Provisional application No. 60/101,828, filed on Sep. 25, 1998, and provisional application No. 60/125,750, filed on Mar. 24, 1999.

(51) Int. Cl.[7] ............................................. A61K 38/12

(52) U.S. Cl. ............................. 514/9; 514/11; 530/317

(58) Field of Search .................................. 424/114, 116; 514/9, 11, 183; 530/317

(56) References Cited

U.S. PATENT DOCUMENTS

| | | | |
|---|---|---|---|
| 4,482,487 A | 11/1984 | Abbott | 530/317 |
| 4,524,135 A | 6/1985 | Abbott | 435/68.1 |
| 4,537,717 A | 8/1985 | Abbott | 530/317 |
| RE32,310 E | 12/1986 | Debono | 530/317 |
| RE32,311 E | 12/1986 | Debono | 530/317 |
| RE32,333 E | 1/1987 | Hamill | 530/317 |
| RE32,455 E | 7/1987 | Hamill | 530/317 |
| 4,800,157 A | 1/1989 | Eaton | 435/71.3 |
| 4,874,843 A | 10/1989 | Baker | 530/317 |
| 4,885,243 A | 12/1989 | Huber | 435/71.3 |
| 5,912,226 A | 6/1999 | Baker | 514/9 |

FOREIGN PATENT DOCUMENTS

| | | |
|---|---|---|
| EP | 0 386 951 | 9/1990 |
| WO | WO 98/22107 | 5/1998 |
| WO | WO 99/30728 | 6/1999 |

OTHER PUBLICATIONS

Richard H. Baltz, "Lipopeptide Antibiotics Produced by *Streptomyces roseosporus* and *Streptomyces fradiae*," *Biotechnology of Antibiotics* 2d Ed., 415–435, 1997.

Boxenbaum et al., "Interspecies Pharmacokinetic Scaling, Biological Design and Neoteny," *Advances in Drug Research* 19: 139–196, 1990.

Caron et al., "Daptomycin or Teicoplanin in Combination with Gentamicin for Treatment of Experimental Endocarditis Due to a Highly Glycopeptide–Resistant Isolate of *Enterococcus faecium*," *Antimicrobial Agents and Chemotherapy* 36:2611–2616, 1992.

Flandrois et al., "Early Stages of In Vitro Killing Curve of LY146032 and Vanomycin for *Staphylococcus aureus*," *Antimicrobial Agents and Chemotherapy* 32:454–457, 1988.

Freireich et al., "Quantitative Comparison of Toxicity of Anticancer Agents in Mouse, Rat, Hamster, Dog, Monkey, and Man," *Cancer Chemotherapy Reports* 50: 219–244, 1966.

Garrison et al., "Suboptimal Effect of Daptomycin in the Treatment of Bacteremias," *Southern Medical Journal* 82: 1414–1415, 1989.

Garrison et al., "Assessment of Effects of Protein Binding or Daptomycin and Vancomycin Killing of *Staphylococcus aureus* by Using an In Vitro Pharmacodynamic Model," *Antimicrobial Agents and Chemotherapy* 34: 1925–1931, 1990.

Gray et al., "Antibiotic–resistant enterococci," *Journal of Hospital Infection* 21:1–14, 1992.

Hanberger et al., "Pharmacodynamics of Daptomycin and Vancomycin in *Enterococcus faecalis* and *Straphylococcus aureus* Demonstrated by Studies of Initial Killing and Post-antibiotic Effect and Influence of $Ca^{2+}$ and Albumin on These Drugs," *Antimicrobial Agents and Chemotherapy* 35: 1710–1716, 1991.

Kaatz et al., "Daptomycin Compared with Teicoplanin and Vancomycin for Therapy of Experimental *Staphylococcus aureus* Endocarditis," *Antimicrobial Agents and Chemotherapy* 34: 2081–2085, 1990.

Lamp et al., "In Vitro Pharmacodynamic Effects of Concentration, pH, and Growth Phase on Serum Bactericidal Activities of Daptomycin and Vancomycin," *Antimicrobial Agents and Chemotherapy* 36: 2709–2714, 1992.

Lee et al., "Daptomycin versus Conventional Therapy in the Treatment of Endocarditis and Bacteremia," *Abstracts of the Interscience Conference on Antimicrobial Agents and Chemotherapy*, A885, 1991.

Lee et al., "Effect of Protein Binding of Daptomycin on MIC and Antibacterial Activity," *Antimicrobial Agents and Chemotherapy* 35: 2505–2508, 1991.

Low et al., "Enterococcis: Pathogens of the 90s," *The European Journal of Surgery Suppl.* 573: 19–24, 1994.

(List continued on next page.)

Primary Examiner—Jose G. Dees
Assistant Examiner—Frank Choi
(74) Attorney, Agent, or Firm—Fish & Neave; James F. Haley, Jr.; Karen E. Brown

(57) ABSTRACT

The invention provides methods for administering a therapeutically effective amount of daptomycin while minimizing skeletal muscle toxicity. The methods provide daptomycin administration at a dosing interval of 24 hours or greater. This long dosing interval minimizes skeletal muscle toxicity and allows for higher peak concentrations of daptomycin, which is related to daptomycin's efficacy. The invention also provides methods of administering lipopeptide antibiotics other than daptomycin while minimizing skeletal muscle toxicity by administering a therapeutically effective amount of the lipopeptide antibiotic at a dosage interval that does not result in muscle toxicity. The invention also provides methods of administering quinupristin/dalfopristin while minimizing skeletal muscle toxicity by administering a therapeutically effective amount of quinupristin/dalfopristin at a dosage interval that does not result in muscle toxicity.

45 Claims, 3 Drawing Sheets

OTHER PUBLICATIONS

Ole–Mapenay et al., "Aspects of the Pharmacokinetics of Doxycycline Given to Healthy and Pneumonic East African Dwarf Goats by Intramuscular Injection," *Veterinary Research Communications* 21: 453–462, 1997.

Prieur et al., "Clinical Toxicologic Evaluation of Cancer Chemotherapeutic Agents: Protocols of the Laboratory of Toxicology," *Cancer Chemotherapy Reports* 4: 1–30, 1973.

Ramos et al., "Comparison of Daptomycin, Vancomycin, and Ampicillin–Gentamicin for Treatment of Experimental Endocarditis Caused by Penicillin–Resistant Enterococci," *Antimicrobial Agents and Chemotherapy* 36: 1864–1869, 1992.

Rotschafer et al., "Therapeutic Update on Glycopeptide and Lipopeptide Antibiotics," *Pharmacotherapy* 8:211–219, 1988.

Rybak et al., "Pharmacokinetics and Bacterial Rates of Daptomycin and Vancomycin in Intravenous Drug Abusers Being Treated for Gram–Positive Endocarditis and Bacteremia," *Antimicrobial Agents and Chemotherapy* 36: 1109–1114, 1992.

Sexton et al., "The Use of Daptomycin, a Lipopeptide Antibiotic, in the Treatment of Gram Positive Infections in Man," *Abstracts of the Interscience Conference on Antimicrobial Agents and Chemotherapy*, A932, 1988.

Stratton et al., "Bactericidal Activity of Deptomycin (LY146032) Compared with Those of Ciprofloxacin, Vanomycin, and Ampicillin against Enterococci as Determined by Kill–Kinetic Studies," *Antimicrobial Agents and Chemotherapy* 31: 1014–1016, 1987.

Stratton et al., "Effect of Human Serum on the Bactericidal Activity of Daptomycin and Vancomycin Against Staphylococcal and Enterococcal Isolates as Determined by Time–Kill Kinetic Studies," *Diagnostic Microbiology and Infectious Disease* 13: 245–252, 1990.

Tally et al., "Daptomycin: a novel agent for Gram–positive infections," *Exp. Opin. Invest Drugs* 8: 1223–1238, 1999.

Thompson, "Dosage Regimen Design: A Pharmacokinetic Approach," *The Journal of Clinical Pharmacology* 32: 210–214, 1992.

Vemuri et al., "Enterococcal infections: The increasing threat of nosocomial spread and drug resistance.," *Journal of Postgraduate Medicine* 93: 121–128, 1993.

Voorn et al., "Role of Tolerance in Treatment and Prophylaxis of Experimental *Staphylococcus areaus* Endocarditis with Vancomycin, Teicoplanin, and Daptomycin," *Antimicrobial Agents and Chemotheraphy* 38: 487–493, 1994.

STN/CAS online, file CAPLUS, Acc. No. 1991:58783, Doc. No. 114:58783, (Leclercq et al., Antimicrob. Agents. Chemother. (1991), 35 (1), pp. 92–98), Abstract.*

STN/CAS online, file DRUGU, Acc. No. 1991–18762, (Rybak et al., Pharmacotherapy (1991), vol. 11, No. 1, p. 98), Abstract.*

STN/CAS online, file EMBASE, Acc. No. 95137070, Doc. No. 1995137070, (Thibault et al., Life Sciences (1995), 56/22, pp. 1877–1887), Abstract.*

STN/CAS online, file EMBASE, Acc. No. 87117940, Doc. No. 1987117940, (Watanakunakorn, Journal of Antimicrobial Chemotherapy (1987), 19/4, pp. 445–448), Abstract.*

Woodworth et al., "Single–Dose Pharmacokinetics and Antibacterial Activity of Daptomycin, a New Lipopeptide Antibiotic, in Healthy Volunteers," *Antimocrobial Agents and Chemotherapy* 36: 318–325, 1992.

Woodworth et al., "Tobramycin and Daptomycin Disposition When Co–Administered to Healthy Volunteers," *Journal of Antimicrobial Chemotherapy* 33:655–659, 1994.

Bernard et al., "Pharmacokinetics and Suction Blister Fluid Penetration of a Semisynthetic Injectable Streptogramin RP59500 (RP 57699/RP54476)," *Eur. J. Clin. Microbiol. Infect. Dis.* 13: 768–771, 1994.

Tally et al., "Daptomycin: A Novel Agent for Gram–Positive Infections," *Exp. Opin. Invest. Drugs* 8:1223–1238, 1999.

Moellering et al., "The Efficacy and Safety of Quinupristin/ Dalfopristin for the Treatment of Infections Caused by Vancomycin–Resistant *Enterococcus faecium,*" *Journal of Antimicrobial Chemotherapy* 44: 251–261, 1999.

STN online, file EMBASE, Acc. No. 90106166, Doc. No. 1990106166 (Pyrka et al. 'Clinical pharmacokinetics of daptomycin', DICP, Annals of Pharmacotherapy, (1990) 24/3 (255–256), Abstract.*

STN online, file EMBASE, Acc. No. 92248249,, Doc. No. 1992248249, (Etienne et al., J. Antimicrobial Chemotherapy, (1992) 30/Supp. A (123–131)), Abstract.*

STN online, file EMBASE, Acc. No. 96269760, Doc. No. 1996269760, (Griswold et al., American J. Health–System Pharmacy, (1996) 53/17 (2045–2053), Abstract.*

STN online, file EMBASE, Acc. No. 89228048, Doc. No. 1989228048 (Kennedy et al., Amtimicrobial Agents and Chemotherapy, (1989) 33/9 (1522–1525)), Abstract.*

STN online, file EMBASE, Acc. No. 89239216, Doc. No. 1989239216 (Van der Auwera, Antimicrobial Agents and Chemotherapy,(1989) 33/10 (1783–1790)), Abstract.*

Remington's Pharmaceutical Sciences (17th Ed. 1985), pp. 1176–1213.*

Bayer, Arnold S., et al., "LY146032 Compared with Penicillin G in Experimental Aortic Valve Endocarditis Caused by Group G Streptococci," *Antimicrobial Agents and Chemotherapy* 32: 141–143 (1988).

Beauchamp, Denis, et al., "Effects of Daptomycin and Vancomycin on Tobramycin Nephrotoxicity in Rats," *Antimicrobial Agents and Chemotherapy* 34: 139–147 (1990).

Black, H.R., et al., "Preliminary Pharmacology and Pharmacokinetics of LY146032, A New Peptolipide Antibiotic," *Program and Abstracts of the 1986 Interscience Conference on Antimicrobial Agents and Chemotherapy*, p. 261, Abstract 894 (1986).

Bush, Larry M., et al., "Daptomycin (LY146032) Treatment of Experimental Enterococcal Endocarditis," *Antimicrobial Agents and Chemotherapy* 32: 877–881 (1988).

Bryant, R.E., et al., "Effect of Abscess Milieu on Bactericidal Activity of LY146032 Against Staphylococci," *Eur. J. Clin. Microbiol.* 6: 186–188 (1987).

Cantoni, L., et al., "Comparative Efficacy of Daptomycin, Vancomycin, and Cloxacillin for the Treatment of *Staphylococcus aureus* Endocarditis in Rats and Role of Test Conditions in this Determination," *Antimicrobial Agents and Chemotherapy* 34: 2348–2353 (1990).

Dougherty, Steven H., et al., "Impact of LY146032 on *Streptococcus (Entoerococcus) faecalis* Translocation in Mice," *Antimicrobial Agents and Chemotherapy* 32: 337–340 (1988).

Dong, Mei–Yan, et al., "Treatment of *Clostridium difficiel* in Hamsters with a Lipopeptide Antibiotic LY 146032," *Antimicrobial Agents and Chemotherapy* 32: 1135–1136 (1987).

Elioppoulos, George M., et al., "In Vitro and In Vivo Activity of LY 146032, a New Cyclic Lipoprotein Antibiotic," *Antimicrobial Agents and Chemotherapy* 30: 532–535 (1986).

Gorbach, Sherwood L., et al., "Treatment of Infectious Diseases," *Infectious Diseases* 2d Ed., 176, 190 (1998).

Haworth, Charles S., et al., "*Staphylococcus aureus* Ventriculitis Treated with Single–Dose Intraventricular Vancomycin or Daptomycin (LY146032): Bacterial and Antibiotic Kinetics in Hydrocephalic Rabbits," *Antimicrobial Agents and Chemotherapy* 34: 245–251 (1990).

Hindes, R.G., et al., "Treatment of Experimental Endocarditis Caused by a β–Lactamase–Producing Strain of *Enterococcus faecalis* with High–Level Resistance to Gentamicin," *Antimicrobial Agents and Chemotherapy* 33: 1019–1022 (1989).

Kephart, Phyllis A., et al., "Comparison of the Investigational Drug, LY 146032 with Vancomycin in Experimental Pneumonia Due to Methicillin–Resistant *Staphylococcus aureus*," *Journal of Antimicrobial Chemotherapy* 21: 33–39 (1988).

Kuechle, David K., et al., "Elution of Vancomycin, Daptomycin, and Amikacin from Acrylic Bone Cement," *Clinical Orthopedics and Related Research* 264: 302–308 (1991).

Leggett, J., et al., Pharmacodynamic and Pharmacokinetic Parameters (PKPs) Affecting Activity of LY 146032 Against *Staphylococcus aureus Program and Abstracts of the 1986 Interscience Conference on Antimicrobial Agents and Chemotherapy*, p. 123, Abstract 154 (1987).

Li, T., et al., "In Vivo Efficacy of Daptomycin Against Systemic Infection Induced by Vancomycin–Resistant *Enterococcus faecalis* (VRE) in the Mouse," *Interscience Conference on Antimicrobial Agents and Chemotherapy*, Abstract F–116 (Sep. 24–27, 1998).

Li, Tongchuan, et al., "Daptomycin Efficacy Against Vancomycin–Resistant *Enterococcus faecalis* (VRE)—Induced Pyelonephritis in the Mouse," *Interscience Conference on Antimicrobial Agents and Chemotherapy*, Poster #1003 (Sep. 26–29, 1999).

Li, Tongchuan, et al., "Effect of Oral Daptomycin on Vancomycin–Resistant *Enterococcus Faecium* (VREF) Gastrointestinal Tract Colonization in Antibiotic Treated Mouse, "Infectious Disease Society of America Meeting, Abstract #244–Sa (Nov. 12–15, 1998).

Louie, Arnold, et al., "The Pharmacodynamics of Daptomycin as Determined for *Staphylococcus aureus* in a Mouse Thigh Infection Model," *Interscience Conference on Antimicrobial Agents and Chemotherapy*, Poster #1770 (Sep. 26–29, 1999).

Luu, Q.N., et al., "Treatment of Chronic Experimental *Staphylococcus aureus* Osteomyelitis with LY146032 and Vancomycin," *Eur. J. Clin. Microbiol. Infect. Dis.* 8: 562–563 (1989).

Mader, Jon T., et al., "Comparative Evaluation of Daptomycin (LY146032) and Vancomycin in the Treatment of Experimental Methicillin–Resistant *Staphylococcus aureus* Osteomyelitis in Rabbits," *Antimicrobial Agents and Chemotherapy* 33: 689–692 (1989).

Michiels, Marie–Jose, et al., "Differential Increased Survival of Staphylococci and Limited Ultrastructural Changes in the Core of Infected Fibrin Clots after Daptomycin Administration," *Antimicrobial Agents and Chemotherapy* 40: 203–211 (1996).

Miniter, Peggy M., et al., "Activity of LY146032 In Vitro and in Experimental Enterococcal Pyelonephritis," *Antimicrobial Agents and Chemotherapy* 31: 1199–1203 (1987).

Nord, C.E., et al., "LY146032 Treatment of *Clostridium difficile Colitis in Hamsters*," *Eur. J. Clin. Microbiol* 6: 686 (1987).

Rice, Louis B., et al., "In Vivo Activity of the Combination of Daptomycin and Fosfomycin Compared with Daptomycin Alone Against a Strain of *Enterococcus faecalis* with High–Level Gentamicin Resistance in the Rat Endocarditis Model," *Diagn. Microbiol. Infect. Dis.* 15: 173–176 (1992).

Safdar, N., et al. "In–Vivo Pharmacodynamic Activity of Daptomycin (DAP) Against Multiple Bacterial Pathogens," *Interscience Conference of Antimicrobial Agents and Chemotherapy*, Poster #1769 (Sep. 26–29, 1999).

Sapico, Francisco L., et al., "LY146032, Alone and in Combination with Gentamicin, for the Treatment of *Enterococcal Pyelonephritis* in the Rat Model," *Antimicrobial Agents and Chemotherapy* 32: 81–83 (1988).

Smith, K., et al., "Daptomycin Versus Vancomycin Treatment for *Staphylococcus Aureus* Bacteremia in a Murine Model," *Chemotherapy* 36: 428–434 (1990).

Verghese, Abraham, et al., "LY146032 in a Hamster Model of *Staphylococcus aureus* Pneumonia: Effect on In Vivo Clearance and Mortality and In Vitro Opsonophagocytic Killing," *Chemotherapy* 34: 497–503 (1988).

Wheat, Lawrence J., et al., "Comparison of Cefazolin, Cefamandole, Vancomycin, and LY146032 for Prophylaxis of Experimental *Staphylococcus epidermidis* Endocarditis," *Antimicrobial Agents and Chemotherapy* 32: 63–67 (1988).

Wood, Craig A., et al., "Influence of Daptomycin on Staphylococcal Abscesses and Experimental Tobramycin Nephrotoxicity," *Antimicrobial Agents and Chemotherapy* 33: 1280–1285 (1989).

Oleson, F.B., et al., "Once–Daily Dosing in Dogs Optimizes Daptomycin Safety," *Antimicrobial Agents and Chemotherapy*, 44: 2948–2953 (2000).

Kennedy et al., "Daptomycin (LY 146032) for prevention and treatment of experimental aortic valve endocarditis in rabbits", Antimicrobial Agents and Chemotherapy (1989), vol. 33, pp. 1522–1525.*

LeClercq et al, Antimicrobial Agents and Chemotherapy (1991), vol. 33, pp. 92–98.*

Watanakunakorn, J. Antimicrobial Chemotherapy (1987), vol. 19, pp. 445–448.*

Thibault et al., Life Sciences (1995), vol. 22, pp. 1877–1887.*

Van der Auwera, Antimicrobial Agents and Chemotherapy (1989), vol. 33, pp. 1783–1790.*

Pryka et al., DICP The Annals of Pharmacotherapy (1990), vol. 24, pp. 255–256.*

* cited by examiner

METHODS FOR ADMINISTRATION OF ANTIBIOTICS

This application claims the benefit of U.S. Provisional Application Nos. 60/101,828, filed Sep. 25, 1998, and 60/125,750, filed Mar. 24, 1999, both of which are herein incorporated by reference.

TECHNICAL FIELD OF THE INVENTION

The present invention relates to improved methods of administering lipopeptide antibiotics, such as daptomycin, with potent bactericidal activity against gram-positive bacteria, including antibiotic-resistant strains. The present invention also relates to improved methods of administering quinopristin/dalfopristin, which also has potent bactericidal activity against gram-positive bacteria, including antibiotic-resistant strains.

BACKGROUND OF THE INVENTION

The rapid increase in the incidence of gram-positive infections—including those caused by resistant bacteria—has sparked renewed interest in the development of novel classes of antibiotics. One such class is the lipopeptide antibiotics, which includes daptomycin. Daptomycin has potent bactericidal activity in vitro against clinically relevant gram-positive bacteria that cause serious and life-threatening diseases. These bacteria include resistant pathogens, such as vancomycin-resistant enterococci (VRE), methicillin-resistant *Staphylococcus aureus* (MRSA), glycopeptide intermediary susceptible *Staphylococcus aureus* (GISA), coagulase-negative staphylococci (CNS), and penicillin-resistant *Streptococcus pneumoniae* (PRSP), for which there are very few therapeutic alternatives (see Tally et al., 1999, Exp. Opin. Invest. Drugs 8:1223–1238, hereafter "Tally"). Daptomycin provides a rapid, concentration-dependent bactericidal effect and a relatively prolonged concentration-dependent post-antibiotic effect in vivo.

Daptomycin is described in Baltz in *Biotechnology of Antibiotics*, 2nd Ed., ed. by W. R. Strohl (New York: Marcel Dekker, Inc.), 1997, pp. 415–435, hereafter "Baltz." Daptomycin is a cyclic lipopeptide antibiotic that can be derived from the fermentation of *Streptomyces roseosporus*. It is comprised of a decanoyl side chain linked to the N-terminal tryptophan of a cyclic 13-amino acid peptide (see FIG. 1a, Baltz et al., supra). The compound is currently being developed in both intravenous and oral formulations to treat serious infections caused by bacteria, including, but not limited to, methicillin resistant *Staphylococcus aureus* (MRSA) and vancomycin resistant enterococci (VRE).

Daptomycin's mechanism of action is distinct from that of other classes of antibiotics, which include β-lactams, aminoglycosides, glycopeptides and macrolides. Without wishing to be bound by any theory, daptomycin is believed to kill gram-positive bacteria by disrupting multiple aspects of bacterial plasma membrane function while not penetrating into the cytoplasm. The antibacterial mechanisms of daptomycin may include inhibition of peptidoglycan synthesis, inhibition of lipoteichoic acid synthesis and dissipation of bacterial membrane potential (see, e.g., Baltz, supra).

The efficacy and safety of daptomycin has been examined in nonclinical studies and in Phase I and Phase II clinical trials. Daptomycin was well tolerated in human volunteers when given intravenously at 1 or 2 mg/kg every 24 hours. See Baltz, supra, and references therein. Furthermore, a single dose of daptomycin was well-tolerated over a dose range of 0.5 to 6 mg/kg. See Baltz, supra, and Woodworth et al., 1992, Antimicrob. Agents Chemother. 36:318–25. However, prolonged treatment with 3 mg/kg daptomycin every 12 hours was shown to cause occasional adverse effects (Baltz, supra). Transient muscular weakness and pain were observed in two of five human patients who had been treated with 4 mg/kg daptomycin every 12 hours for 6 to 11 days (Tally, supra). In the two subjects who experienced muscular weakness and pain, creatine phosphokinase (CPK) levels had increased one to two days prior to the muscular weakness. Treatment was discontinued three to four days after the initial elevation in CPK was observed. One to two days after discontinuation of daptomycin treatment, CPK levels peaked at levels in excess of 10,000 U/L in one subject and at 20,812 U/L in the second subject (Tally, supra). Based upon these studies and the rationale that higher doses of daptomycin were required for efficacy against many types of bacterial infection, clinical studies of daptomycin were discontinued (Baltz, supra).

In the above-described clinical trials and in a series of toxicology studies in animals, skeletal muscle was found to be the primary target tissue of daptomycin toxicity. Repeated daily intravenous administration in toxicological studies of high doses of daptomycin in rats and dogs (75 mg/kg/day in rats and 40 mg/kg/day in dogs) caused mild myopathy in the skeletal muscle (Tally, supra). It was also found that increases in CPK levels are a sensitive measure of myopathy, and thus can be used to measure daptomycin's effects upon muscle tissue. See Tally et al. supra.

Although low doses of daptomycin do not cause muscle toxicity and are effective in treating many gram-positive bacterial infections, certain types of gram-positive bacterial infections, such as deep-seated infections or those caused by certain antibiotic-resistant bacterial strains, may require higher doses of daptomycin for effective treatment. For instance, certain vancomycin-resistant strains of bacteria exhibit a two- to four-fold higher daptomycin minimum inhibitory concentration (MIC) than most vancomycin-susceptible strains. Accordingly, there is a great need to develop methods for administration of effective amounts of daptomycin that will also minimize adverse skeletal muscle effects.

A non-lipopeptide streptogramin antibiotic combination, quinupristin/dalfopristin, has also shown activity against gram-positive organisms, including antibiotic-resistant bacteria such as methicillin-resistant *Staphylococcus aureus*, glycopeptide intermediary *S. aureus*, and glycopeptide-resistant *Enterococcus faecium* (Rubinstein et al., 1999, J. Antimicrob. Chemother. 44, Topic A, 37–46, hereafter "Rubinstein"). Quinupristin/dalfopristin has been shown to be effective in treatment of nosocomial pneumonia, emergency use studies, complicated skin and skin structure infection and bacteremia (Rubinstein, supra). Approximately 13% of the patients treated with 7.5 mg/kg quinupristin/dalfopristin every 8 or 12 hours experienced arthralgia or myalgia, which included muscle pain, and approximately 5% of patients exhibited increased CPK levels (Rubinstein, supra). Therefore, it would appear that quinupristin/dalfopristin also causes muscle toxicity.

The aminoglycosides, which make up another class of antibiotics, are also toxic at high doses. They have been administered as a high dose at less frequent intervals rather than at lower doses at more frequent intervals in order to reduce their toxicity (Barclay et al., 1994, Clin. Pharmacokinet. 27:32–48). However, aminoglycosides differ from daptomycin in a number of ways, specifically in the fact that the sites of toxicity are distinct. Aminoglycosides are toxic to the kidney and central nervous system whereas skeletal muscle is the site of toxicity for daptomycin. The mechanisms of toxicity for aminoglycosides and daptomycin are also distinct. In addition, aminoglycosides are structurally dissimilar to daptomycin, act only on gram-negative bacteria, have a different mechanism of antibacterial action from daptomycin and exhibit different mechanisms of resistance. Thus, the possibility that less frequent administration of aminoglycosides results in lower toxicity to the patient does not predict that the same would be true for daptomycin.

SUMMARY OF THE INVENTION

The present invention addresses the problem of skeletal muscle toxicity at high doses of lipopeptide antibiotics such as daptomycin, as well as quinupristin/dalfopristin. The invention provides methods for administering the antibiotic that minimizes skeletal muscle toxicity while simultaneously maintaining a sufficient efficacy level.

The process of the invention is characterized by administering less frequent doses comprising a higher concentration of an antibiotic. This protocol is both safer and more efficacious than administering more frequent doses of the antibiotic at lower concentrations. Thus, in one method of the invention, daptomycin is administered to a patient in need thereof at a dosing interval that minimizes skeletal muscle toxicity. In another method of the invention, a lipopeptide antibiotic other than daptomycin, such as a daptomycin derivative, A54145 or a derivative thereof, is administered to a patient in need thereof at a dosing interval that minimizes skeletal muscle toxicity. In a third method of the invention, quinupristin/dalfopristin is administered to a patient in need thereof at a dosing interval that minimizes skeletal muscle toxicity.

The methods of the invention are characterized by administering a high dose of an antibiotic that causes skeletal muscle toxicity at a dosage interval of 24 hours to once weekly. In one embodiment of the invention, daptomycin is administered at a dose of 3 to 75 mg/kg at a dosage interval of 24 hours to once weekly. In another embodiment of the invention, quinupristin/dalfopristin is administered at a dose of 7.5 to 75 mg/kg at a dosage interval of 24 hours to once weekly.

DETAILED DESCRIPTION OF THE INVENTION

To investigate the potential effects of dose fractionation on toxicity, two studies were conducted in dogs comparing the effects of repeated intravenous administration once daily (q24h) versus every 8 hours (q8h). These studies were conducted in the dog since this species is most predictive of clinical effects. The objective of the studies was to assess the relationship between pharmacokinetics, including $C_{max}$ and $AUC_{24h}$, and skeletal muscle toxicity, in order to determine the optimal clinical dosing regimen to minimize potential for skeletal muscle toxicity.

Figure 2A:
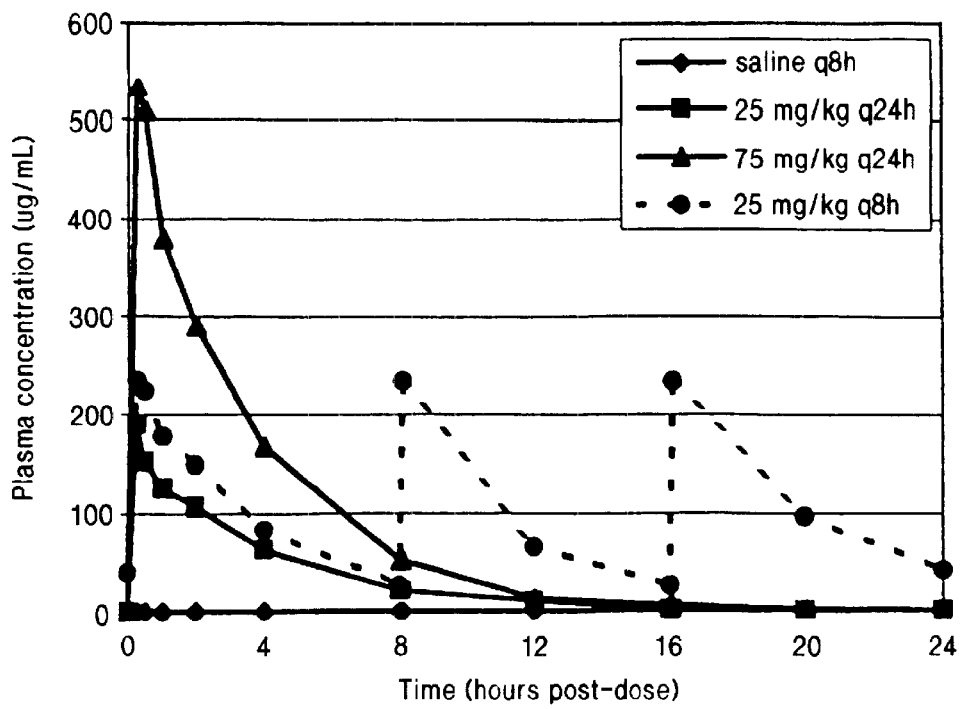
FIGS. 2A and 2B. Steady state plasma concentrations of daptomycin on day 18 of dosing as determined by HPLC for Dog Study A (FIG. 2A) and Dog Study B (FIG. 2B).

Study A explored whether daptomycin-related skeletal muscle toxicity is related to the peak concentration of daptomycin that occurs in the bloodstream after administration ($C_{max}$) and not to the total concentration of daptomycin in the bloodstream for 24 hours ($AUC_{24h}$). In Study A, the daptomycin daily dose was fractionated into multiple administrations per day to reduce $C_{max}$ (see Example 1 and FIG. 2A).

Study B examined whether a threshold plasma concentration exists for daptomycin-related skeletal muscle toxicity. Under this hypothesis, administration of the no observed effect dose level at 24 hours (NOELq24h) multiple times per day, such that plasma levels of daptomycin remain below some undetermined threshold of toxicity, would not be associated with skeletal muscle toxicity (Example 2).

Surprisingly, muscle toxicity was not primarily related to $C_{max}$. For example, both serum creatine phosphokinase (CPK) levels and the incidence of microscopic myopathy observed at 25 mg/kg administered once every 8 hours (q8h) were greater than those observed at 75 mg/kg administered once every 24 hours (q24h), despite the lower $C_{max}$ for 25 mg/kg q8h (Example 1, Table 2). In contrast, large increases in peak CPK levels were observed when the dose interval was varied from q24h to q8h at a dose of either 5 mg/kg or 25 mg/kg even though $C_{max}$ levels were comparable for each dose at either q24h or q8h (Example 1, Table 2 and Example 2, Table 4). Toxicity also did not appear to be related to $AUC_{24h}$, since the toxicity observed at 25 mg/kg q8h was greater than at 75 mg/kg q24h at approximately the same AUC.

Figure 3:
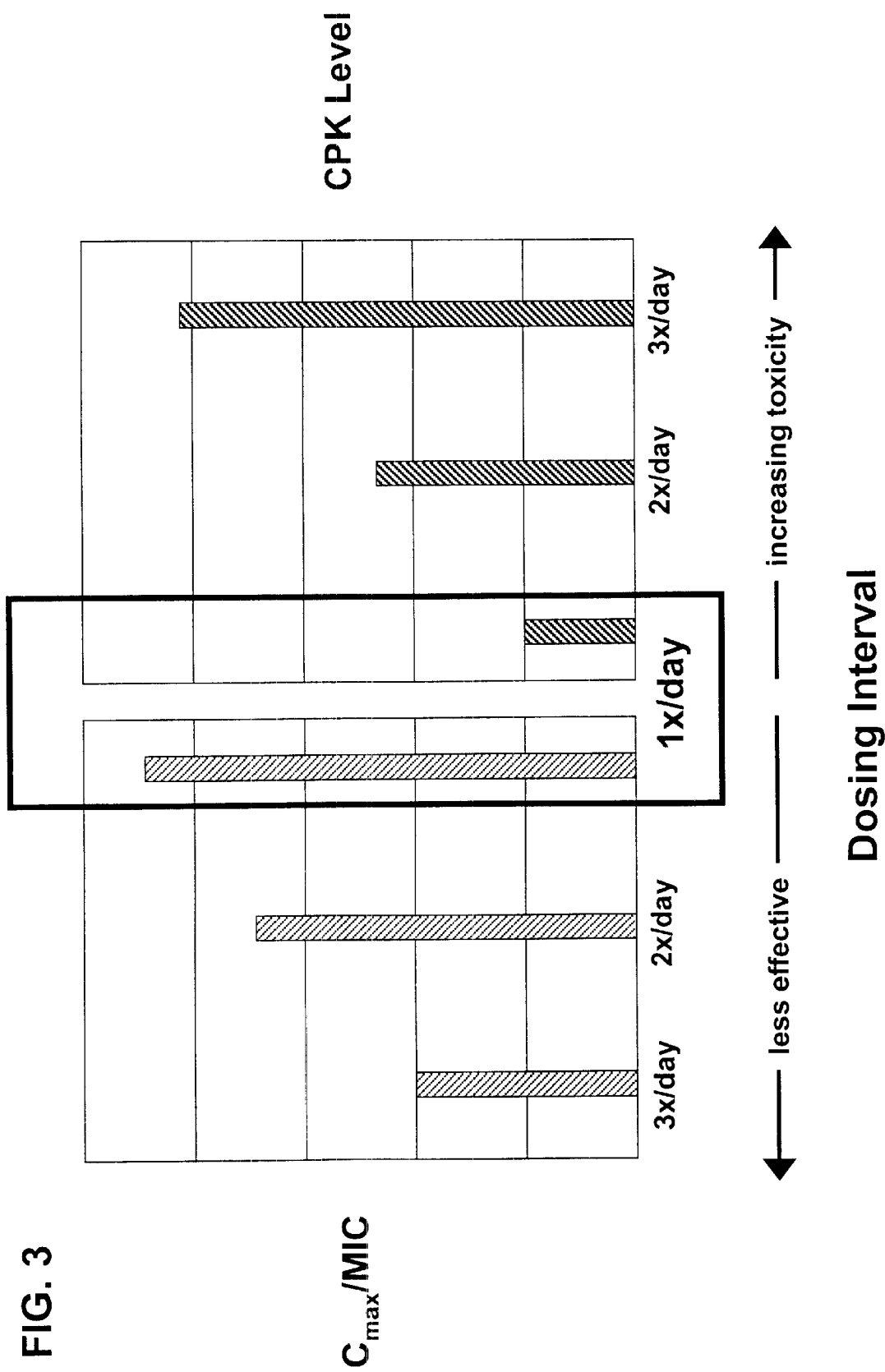
FIG. 3. Relationship between different dosing intervals of daptomycin and its skeletal muscle toxicity (related to CPK levels) and its effectiveness (related to the peak serum concentration, $C_{max}$, over the minimal inhibitory concentration, MIC, of daptomycin).

The results of Studies A and B suggest that the pharmacokinetic parameter defining daptomycin-associated skeletal muscle toxicity in dogs is not related to $C_{max}$. In addition, toxicity did not appear to be related to AUC or an intrinsically toxic plasma concentration, but appeared to be related to the dosing interval of daptomycin. Without wishing to be bound by any theory, skeletal muscle effects appear to be related to the duration of time at low plasma concentrations of daptomycin available for repair of subclinical damage to the myofibers. Therefore, the data suggest that the dosing interval is the key determinant of muscle toxicity, rather than just the magnitude of the dose itself. Further, since $C_{max}$ and/or AUC were found to be the key pharmacokinetic parameters associated with eradication of infection (J. Leggett et al., Abstract No. 154, page 123, Program and Abstracts of the 27th Interscience Conference on Antimicrobial Agents and Chemotherapy, American Society for Microbiology, Washington, D.C., 1987; A. Louie et al., Abstract No. 1769, N. Safdar et al., Abstract No. 1770, Program and Abstracts of the 39th Interscience Conference on Antimicrobial Agents and Chemotherapy, American Society for Microbiology, San Francisco, Calif., Sep. 26–29, 1999), the pharmacological activity of daptomycin is optimized by once-daily dosing. These results suggest that once-daily dosing can minimize daptomycin muscle toxicity, while potentially optimizing its antimicrobial efficacy (FIG. 3).

These observations are further supported by the results of a clinical study. The study demonstrated that daptomycin administered at doses of 4 mg/kg q24h, 6 mg/kg q24h or at an initial dose of 6 mg/kg with subsequent doses at 3 mg/kg q12h did not result in an increase in CPK levels related to daptomycin administration and did not result in any muscle weakness or pain in any patient (Example 4). The $C_{max}$ is predicted to be higher (86.8 µg/mL) at a dose regimen of 6 mg/kg q24h than at a dose regimen of 4 mg/kg q12h (69.2 µg/mL). Yet zero of nine patients tested at the dose regimen predicting a higher $C_{max}$ had drug related adverse skeletal muscle effects (Table 5), whereas two of five patients tested at the dose regimen predicting a lower $C_{max}$ had adverse skeletal muscle effects (Tally, supra). Thus, the results presented in Example 3 demonstrate that $C_{max}$ is not the cause of skeletal muscle toxicity in humans, further showing that the findings regarding daptomycin dosing in dogs is applicable to humans.

Figure 1A:
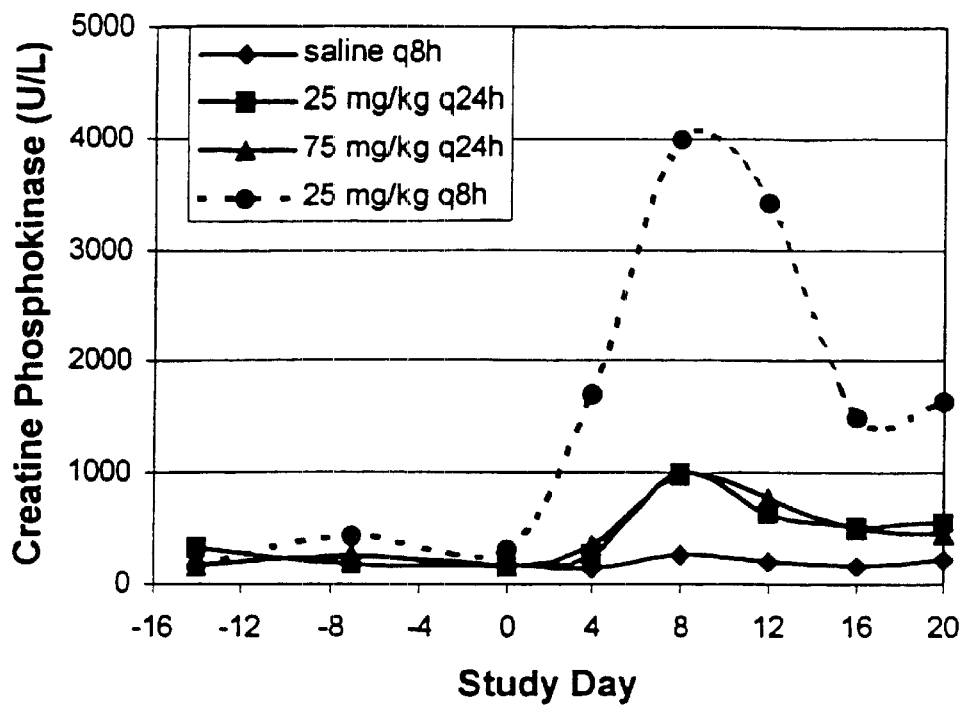
FIGS. 1A and 1B. Serum creatine phosphokinase (CPK) levels for Dog Study A (FIG. 1A) and Dog Study B (FIG. 1B). Serum CPK levels were determined at two hours after daptomycin dosing as an indication of muscle toxicity.
Figure 1B:
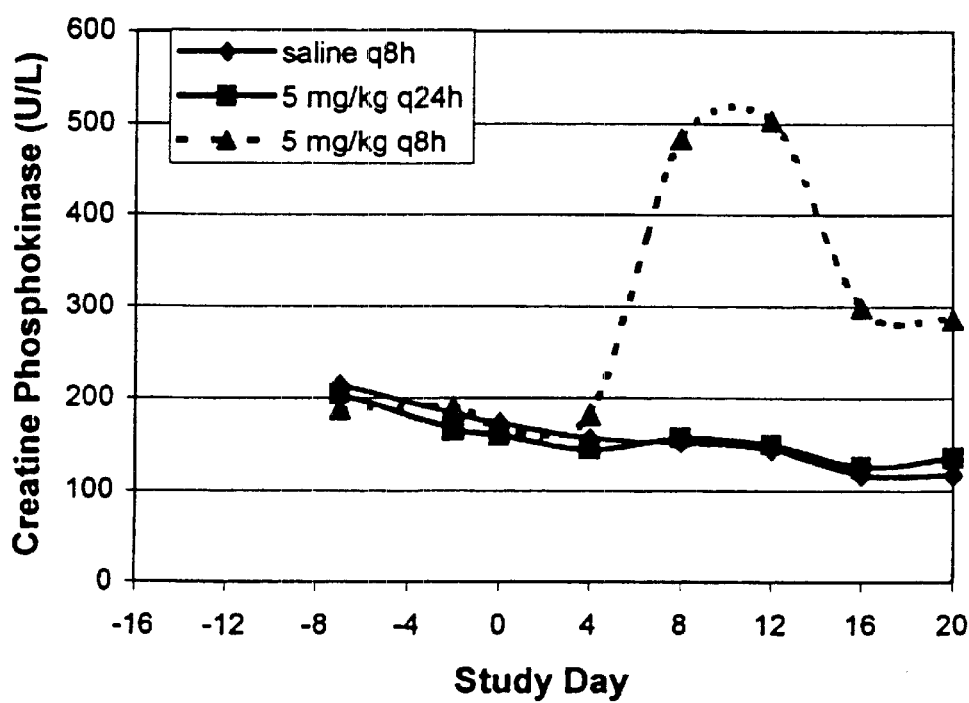

Without wishing to be being bound by any theory, these results may be explained by the hypothesis that skeletal muscle toxicity is related to time between doses for repair of skeletal muscle damage. For instance, Example 1 demonstrates that CPK levels were much higher when dogs were administered 75 mg/kg/day fractionated into three doses per day (25 mg/kg q8h), than when the same dose was administered once per day (75 mg/kg q24h). Once-daily administration may allow greater time between doses (at non-toxic blood levels) for repair of subclinical muscle damage associated with daptomycin. Thus, once-daily dosing results in less toxicity. The new repair hypothesis is consistent with the lack of progression of toxicity after extended durations of dosing. For instance, there is no progression of toxicity for six-month dosing studies compared to one-month dosing studies in rats and dogs. In addition, the new repair hypothesis is consistent with observations that CPK levels decrease despite continued treatment with daptomycin and the presence of regenerative changes in skeletal muscle (FIGS. 1A and 1B). In addition, because $C_{max}$ and/or AUC are the key determinants of efficacy in animal models of infection, the pharmacological activity of daptomycin is optimized by once-daily dosing. Therefore, because safety and efficacy are not dependent upon the same determinant ($C_{max}$), the safety margin for daptomycin can be increased by altering the dosing regimen.

Based upon these results, the present invention provides methods for administering daptomycin that minimize skeletal muscle toxicity compared to prior methods for administering daptomycin. The methods may be used for human patients in clinical applications and in veterinary applications. The dose and dosage interval for the method is one that is safe and efficacious in clinical or veterinary applications. The method of the invention teaches, in general, that longer dosing intervals can provide for the administration of higher doses of daptomycin.

In one embodiment of the instant invention, the dose is 3 to 75 mg/kg daptomycin. In a preferred embodiment, the dose is 6 to 25 mg/kg. In a more preferred embodiment, the dose for humans patients is 6 to 12 mg/kg. Doses that may be used include 7, 8, 9, 10, 11, 12, 14, 16, 18, 20, 22 or 25 mg/kg. In a preferred embodiment for veterinary applications, the dose is 3 to 25 mg/kg. Other doses higher than, intermediate to or less than these doses may also be used and may be determined by one skilled in the art following the methods of this invention.

In one embodiment of the instant invention, the dosage interval is 24 hours to once weekly. In a preferred embodiment, daptomycin is administered at a dosage interval of once every 24 hours, once every 48 hours, once every 72 hours, once every 96 hours, or once weekly. Administration at less frequent dosage intervals, such as once every 96 hours or once weekly, may be desirable for patients who have impaired renal function or who require hemodialysis. In a more preferred embodiment the dosage interval is 24 to 48 hours. In an even more preferred embodiment, the dosage interval is 24 hours. The preferred dosage interval for veterinary applications may be somewhat shorter or longer than the preferred dosage intervals for human patients, depending upon whether daptomycin has a shorter or longer half-life, respectively, in a particular animal species than in humans. The present invention also provides a use of daptomycin for the preparation of medicaments for treating a bacterial infection in a patient at the doses and dosage intervals described herein. Other dosage intervals intermediate to or shorter than these dosage intervals for both clinical and veterinary applications may also be used and may be determined by one skilled in the art following the methods of this invention.

In one embodiment of the invention, the method comprises the step of administering a dose of 3 to 75 mg/kg daptomycin once every 24 hours to once weekly. In a preferred embodiment, daptomycin is administered in a dose of 3 to 25 mg/kg once every 24, 48, 72 or 96 hours. In a more preferred embodiment, daptomycin is administered to a human patient in a dose of 3 to 12 mg/kg every 24 to 48 hours. In an even more preferred embodiment, daptomycin is administered in a dose of 3, 4, 5, 6, 7, 8, 9, 10, 11 or 12 mg/kg once every 24 hours. In veterinary applications, daptomycin is administered in a dose of 3 to 25 mg/kg every 24 hours.

Daptomycin may be administered according to this method until the bacterial infection is eradicated or reduced. In one embodiment, daptomycin is administered for a period of time from 3 days to 6 months. In a preferred embodiment, daptomycin is administered for 7 to 56 days. In a more preferred embodiment, daptomycin is administered for 7 to 28 days. In an even more preferred embodiment, daptomycin is administered for 7 to 14 days. Daptomycin may be administered for a longer or shorter time period if it is so desired.

Furthermore, although the invention has been exemplified using daptomycin, the results and the method of the instant invention are also applicable to other lipopeptide antibiotics and quinupristin/dalfopristin, or other antibiotics that cause skeletal muscle toxicity. Therefore, the present invention also provides methods for administering other lipopeptide antibiotics that minimize skeletal muscle toxicity while maintaining efficacy. The present invention also provides a use for lipopeptide antibiotics for the preparation of medicaments for treating a bacterial infection in a patient, wherein the dose is a therapeutically effective amount of the lipopeptide antibiotic at a dosage interval that does not result in muscle toxicity. Lipopeptide antibiotics include, without limitation, daptomycin, daptomycin derivatives, and other antibiotics that comprise a proteinaceous domain and a lipid domain, such as A54145 (Baltz, supra), or A54145 derivatives.

The present invention also provides methods for administering quinupristin/dalfopristin that minimize skeletal muscle toxicity while maintaining efficacy. The methods may be used for human patients in clinical applications and in veterinary applications. The dose and dosage interval for the method is one that is safe and efficacious in clinical or veterinary applications. The method of the invention teaches, in general, that a higher dose of quinupristin/dalfopristin can be administered by prolonging the dosing interval. In one embodiment, the dose is 7.5 to 75 mg/kg quinupristin/dalfopristin at a dosage interval of 24 hours to once weekly. In a preferred embodiment, the dose is 7.5 to 30 mg/kg. In a more preferred embodiment, the dose for humans patients is 7.5 to 20 mg/kg. In a more preferred embodiment for veterinary applications, the dose is 7.5 to 50 mg/kg. In a preferred embodiment, the dosage interval is 24, 48, 72 or 96 hours. In a more preferred embodiment the dosage interval is 24 hours. The preferred dosage interval for veterinary applications may be somewhat shorter or longer than the preferred dosage intervals for human patients, depending upon whether quinupristin/dalfopristin has a shorter or longer half-life, respectively, in a particular animal species than in humans. The present invention also provides a use for quinupristin/dalfopristin for the preparation of medicaments for treating a bacterial infection in a patient, wherein the dose is a therapeutically effective amount of quinupristin/dalfopristin at a dosage interval that does not result in muscle toxicity.

The methods of the present invention comprise administering daptomycin, other lipopeptide antibiotics or quinupristin/dalfopristin to a patient in need thereof an amount that is efficacious in reducing or eliminating the gram-positive bacterial infection and that results in reduced skeletal muscle toxicity compared to other methods of administering daptomycin, other lipopeptide antibiotics or quinupristin/dalfopristin. The antibiotic may be administered orally, parenterally, by inhalation, topically, rectally, nasally, buccally, vaginally, or by an implanted reservoir, external pump or catheter. Daptomycin, other lipopeptide antibiotics or quinupristin/dalfopristin also may be directly injected or administered into an abscess, ventricle or joint. Parenteral administration includes subcutaneous, intravenous, intramuscular, intra-articular, intra-synovial, cisternal, intrathecal, intrahepatic, intralesional and intracranial injection or infusion. In a preferred embodiment, the antibiotic administration is via intravenous, subcutaneous or oral administration.

The methods according to the instant invention may be used to treat a patient having a bacterial infection in which the infection is caused or exacerbated by any type of gram-positive bacteria. In a preferred embodiment, daptomycin, a lipopeptide antibiotic or quinupristin/dalfopristin is administered to a patient according to the methods of this invention. In another preferred embodiment, the bacterial infection may be caused or exacerbated by bacteria including, but not limited to, methicillin-susceptible and methicillin-resistant staphylococci (including *Staphylococcus aureus, Staphylococcus epidermidis, Staphylococcus haemolyticus, Staphylococcus hominis, Staphylococcus saprophyticus*, and coagulase-negative staphylococci), glycopeptide intermediary-susceptible *Staphylococcus aureus* (GISA), penicillin-susceptible and penicillin-resistant streptococci (including *Streptococcus pneumoniae, Streptococcus pyogenes, Streptococcus agalactiae, Streptococcus avium, Streptococcus bovis, Streptococcus lactis, Streptococcus sangius* and Streptococci Group C, Streptococci Group G and viridans streptococci), enterococci (including vancomycin-susceptible and vancomycin-resistant strains such as *Enterococcus faecalis* and *Enterococcus faecium*), *Clostridium difficile, Clostridium clostridiiforme, Clostridium innocuum, Clostridium perfringens, Clostridium ramosum, Haemophilus influenzae, Listeria monocytogenes, Corynebacterium jeikeium*, Bifidobacterium spp., *Eubacterium aerofaciens, Eubacterium lentum, Lactobacillus acidophilus, Lactobacillus casei, Lactobacillus plantarum*, Lactococcus spp., Leuconostoc spp., Pediococcus, *Peptostreptococcus anaerobius, Peptostreptococcus asaccarolyticus, Peptostreptococcus magnus, Peptostreptococcus micros, Peptostreptococcus prevotii, Peptostreptococcus productus, Propionibacterium acnes*, and Actinomyces spp.

The antibacterial activity of daptomycin against classically "resistant" strains is comparable to that against classically "susceptible" strains in in vitro experiments. In addition, the minimum inhibitory concentration (MIC) value for daptomycin against susceptible strains is typically 4-fold lower than that of vancomycin. Thus, in a preferred embodiment, daptomycin is administered according to the methods of this invention to a patient who exhibits a bacterial infection that is resistant to other antibiotics, including vancomycin. In addition, unlike glycopeptide antibiotics, daptomycin exhibits rapid, concentration-dependent bactericidal activity against gram-positive organisms. Thus, in a preferred embodiment, daptomycin is administered according to the methods of this invention to a patient in need of rapidly acting antibiotic therapy. Quinupristin/dalfopristin is also useful for treating antibiotic-resistant strains of bacteria, and may be used in emergency use situations.

The methods of the instant invention may be used for a gram-positive bacterial infection of any organ or tissue in the body. These organs or tissue include, without limitation, skeletal muscle, skin, bloodstream, kidneys, heart, lung and bone. The methods of the invention may be used to treat, without limitation, skin and soft tissue infections, bacteremia and urinary tract infections. The methods of the invention may be used to treat community acquired respiratory infections, including, without limitation, otitis media, sinusitis, chronic bronchitis and pneumonia, including pneumonia caused by drug-resistant *Streptoococcus pneumoniae* or *Haemophilus influenzae*. The methods of the invention may be used to treat mixed infections that comprise different types of gram-positive bacteria, or which comprise both gram-positive and gram-negative bacteria. These types of infections include intra-abdominal infections and obstetrical/gynecological infections. The methods of the invention may be used in step down therapy for hospital infections, including, without limitation, pneumonia, intra-abdominal sepsis, skin and soft tissue infections and bone and joint infections. The methods of the invention also may be used to treat an infection including, without limitation, endocarditis, septic arthritis and osteomyelitis. In a preferred embodiment, any of the above-described diseases may be treated using daptomycin according to the methods of the instant invention. In another preferred embodiment, any of the above-described diseases may be treated using a lipopeptide antibiotic or quinupristin/dalfopristin according to the methods of the instant invention.

The methods of the instant invention may also be practiced while concurrently administering one or more antibiotics other than a lipopeptide antibiotic. Daptomycin exhibits high plasma protein binding and is unable to cross cell membranes. Thus, daptomycin and other lipopeptide antibiotics that exhibit these characteristics are unlikely to cause interactions with other antibiotics. Given this profile, daptomycin would be expected to work synergistically with one or more co-administered antibiotics. Furthermore, daptomycin may improve the toxicity profile of one or more co-administered antibiotics. It has been shown that administration of daptomycin and an aminoglycoside may ameliorate renal toxicity caused by the aminoglycoside. Quinupristin/dalfopristin may also be administered according to this invention with certain other antibiotics. Quinupristin/dalfopristin inhibits cytochrome P450 3A4-mediated metabolism of certain drugs, such as midazolam, nifedipine, terfenadine and cyclosporin, so these drugs should not be co-adminstered with quinupristin/dalfopristin. In a preferred embodiment, an antibiotic may be administered concurrently while practicing the method of this invention. Antibiotics and classes thereof that may be co-administered with daptomycin or another lipopeptide antibiotic include, without limitation, penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone and viomycin. In a preferred embodiment, antibiotics that may be co-administered with daptomycin or other lipopeptide antibiotics according this invention include, without limitation, imipenen, amikacin, netilmicin, fosfomycin, gentamicin, ceftriaxone and teicoplanin.

EXAMPLE 1

STUDY A: EFFECT OF $C_{MAX}$ ON CPK AND SKELETAL MUSCLE TOXICITY

In order to study the effects of $C_{max}$ on skeletal muscle toxicity, dogs (4 male dogs/group) were administered dose regimens of saline q8h, daptomycin 25 mg/kg q24h, daptomycin 75 mg/kg q24h and daptomycin 25 mg/kg q8h intravenously for 20 days. Skeletal muscle toxicity was measured in dogs by increases in CPK levels to above the normal range and by microscopic changes in skeletal tissue.

Figure 2B:
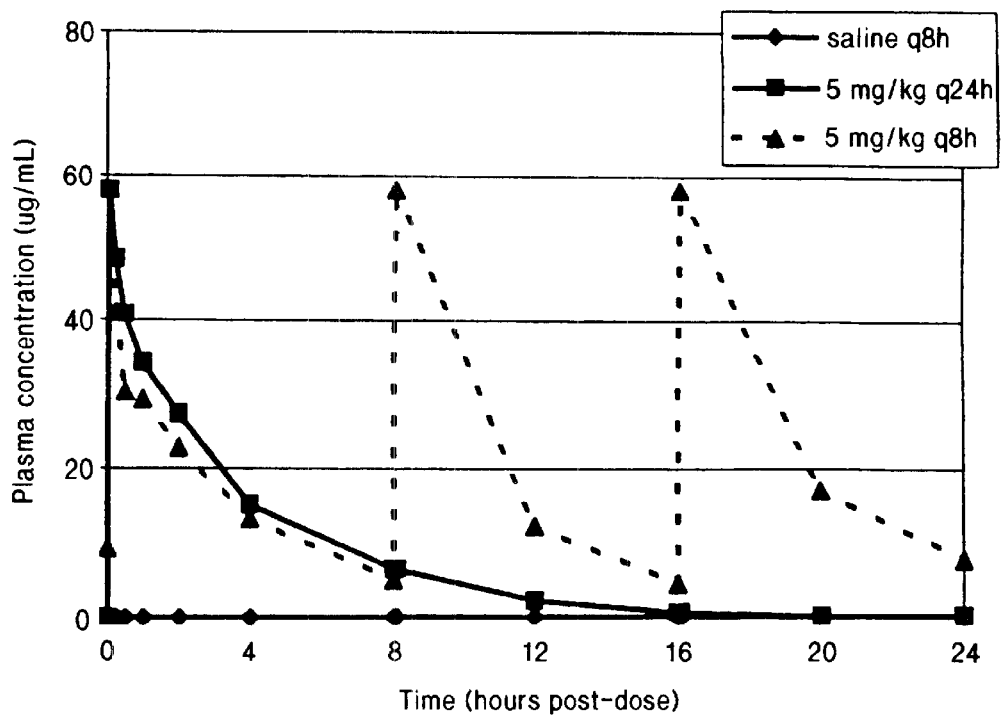

Steady state plasma concentrations of daptomycin on day 18 of dosing were determined by HPLC. $C_{max}$ levels were approximately the same (1.23-fold higher) at 25 mg/kg q8h compared to 25 mg/kg q24h. $C_{max}$ levels were approximately 2.8-fold higher at 75 mg/kg q24h compared to 25 mg/kg q8h. See FIG. 1A (Study A). The AUC was approximately the same (0.37-fold higher) at 25 mg/kg q8h compared to 75 mg/kg q24h (see Table 2 and FIG. 2, top panel).

Throughout the treatment period in Study A, a dose-proportional increase in peak CPK activity was apparent when the dose was increased from 25 to 75 mg/kg at a constant q24h dosing interval. However, an additional 4-fold increase in CPK levels were observed in animals dosed at 25 mg/kg q8h as compared with those dosed at 75 mg/kg q24h, even though the total daily dose for these two regimens was the same. For all dose regimens, CPK peaked after approximately 1 week of treatment, then declined despite continued treatment.

Treated animals were sacrificed at approximately one dosing interval after the last dose and muscle tissue was microscopically examined for indications of myopathy. See Table 1.

TABLE 1

| Site | Dose Regimen | | | |
|---|---|---|---|---|
| Lesion* | Saline q8h | 25 mg/kg q24h | 75 mg/kg q24h | 25 mg/kg q8h |
| Skeletal muscle | | | | |
| Myofiber degeneration | 0/24 | 3/24 | 8/24 | 14/24 |
| Myofiber regeneration | 1/24 | 2/24 | 1/24 | 9/24 |

TABLE 1-continued

| Site | Dose Regimen | | | |
|---|---|---|---|---|
| Lesion* | Saline q8h | 25 mg/kg q24h | 75 mg/kg q24h | 25 mg/kg q8h |
| Diaphragm | | | | |
| Myofiber degeneration | 0/4 | 0/4 | 0/4 | 1/4 |
| Heart | | | | |
| Myofiber degeneration | 0/4 | 0/4 | 0/4 | 0/4 |

*The incidence of muscle-related histopathological findings is presented as the number of sites affected divided by the number of sites examined. For skeletal muscle, six sites were examined in each of four dogs for a total of 24 sites.

Skeletal myofiber degeneration increased approximately two-fold at 25 mg/kg q8h compared to 75 mg/kg q75h. In addition, skeletal myofiber degeneration increase five-fold at 25 mg/kg q8h compared to 25 mg/kg q24h. The skeletal myofiber degeneration was of minimal severity, correlating to three- to 25-fold increases in serum CPK. No microscopic degenerative effect on heart muscle was observed in Study A.

The findings of Study A are summarized in Table 2:

TABLE 2

| Dose Regimen | Total Daily Dose (mg/kg) | $C_{max}$ (μg/mL) | $AUC_{0-24\,h}$ (μg-h/mL) | Peak CPK (U/L) | Incidence of Microscopic Myopathy[1] |
|---|---|---|---|---|---|
| saline q8h | 0 | 0 | 0 | 265 | 0/28 |
| 25 mg/kg q24h | 25 | 190 | 682 | 309* | 3/28 |
| 75 mg/kg q24h | 75 | 540 | 1840 | 990 | 8/28 |
| 25 mg/kg q8h | 75 | 238 | 2526 | 4000 | 15/28 |

*Outlier excluded.
[1]The incidence of microscopic myopathy (last column) shows the number of sites that exhibit minimal degenerative changes divided by the number of sites examined. In this experiment, seven sites were examined in each of four dogs for a total of 28 sites.

In addition, toxicity did not appear to be related to $AUC_{0-24h}$ or a nontoxic plasma concentration threshold. Increases in CPK and incidence of myopathy were greater at 25 mg/kg q8h than at 75 mg/kg q24h despite the lower $C_{max}$. Further, there was a 5-fold increase in toxicity as measured by the incidence of microscopic myopathy and a greater than 10-fold increase in CPK levels when 25 mg/kg was administered three times a day compared to once daily despite comparable $C_{max}$ levels. Although the AUC was only 0.37-fold higher at a dose regimen of 25 mg/kg q8h as compared to 75 mg/kg q24h, CPK activity and incidence of myopathy increased 2- to 4-fold.

Without wishing to be bound by any theory, skeletal muscle effects appear to be related to the duration of time at low plasma concentrations available for repair of subclinical damage to the myofibers. In comparison to dose fractionation, once-daily dosing resulted in greater time at minimal plasma concentrations, allowing for more time for repair and, therefore, less toxicity. For example, at a dose regiment of 25 mg/kg q8h, the plasma concentrations never fell below 27 μg/mL, the trough value for this regimen. In contrast, plasma concentrations for the 75 mg/kg q24h regimen were below this level for approximately 12 hours prior to administration of the next dose. This daily period of minimal exposure may explain why the once-daily dosing regimen (75 mg/kg q24h) was associated with less toxicity than fractionated dosing (25 mg/kg q8h).

EXAMPLE 2

STUDY B: EFFECT OF THRESHOLD PLASMA CONCENTRATION ON SKELETAL MUSCLE TOXICITY

In order to study the effects of threshold plasma concentration on skeletal muscle toxicity, dogs (4 male dogs/group) were administered dose regimens of saline q8h, daptomycin 5 mg/kg q24h (approximate NOELq24h) and daptomycin 5 mg/kg q8h intravenously for 20 days.

As in Example 1, steady state plasma concentrations of daptomycin on day 18 of dosing were determined by HPLC. The q8h interval represents 3 half-lives in dogs ($t_{1/2}$=2.5 hours) and should have minimal impact on steady state $C_{max}$ as compared to a q24h regimen. The $C_{max}$ for 5 mg/kg q8h and 5 mg/kg q24h was approximately the same for both dose regimens. See FIG. 1B (Study B). However, the AUC was approximately three-fold higher (2.6-fold higher) at 5 mg/kg q8h compared to 5 mg/kg q24h (see Table 4 and FIG. 2B).

Serum CPK levels were determined as disclosed in Example 1. There were no changes in CPK levels at 5 mg/kg q24h compared to the saline control. In contrast, CPK levels at 5 mg/kg q8h were elevated compared to 5 mg/kg q24h or saline controls. At 5 mg/kg q8h, CPK levels peaked at levels three-to four-fold higher than baseline after one week of daptomycin treatment, and declined thereafter despite continued treatment, similar to what was seen in Study A. See FIG. 1B (Study B).

Treated animals were sacrificed at approximately one dosing interval after the last dose and muscle tissue was examined microscopically for indications of myopathy as in Example 1, shown in Table 3.

TABLE 3

| Site Lesion* | Dose Regimen | | |
|---|---|---|---|
| | Saline q8h | 5 mg/kg q24h | 5 mg/kg q8h |
| Skeletal muscle | | | |
| Myofiber degeneration | 0/24 | 2/24 | 11/24 |
| Myofiber regeneration | 0/24 | 3/24 | 18/24 |
| Diaphragm | | | |
| Myofiber degeneration | 0/4 | 1/4 | 0/4 |
| Heart | | | |
| Myofiber degeneration | 0/4 | 0/4 | 0/4 |

*The incidence of muscle-related histopathological findings is presented as the number of sites affected divided by the number of sites examined. For skeletal muscle, six sites were examined in each of four dogs for a total of 24 sites.

Skeletal myofiber degeneration increased four-fold at 5 mg/kg q8h compared to 5 mg/kg q24h. Degeneration was of very minimal severity with very few fibers affected, correlating with zero- to four-fold increases in CPK levels. The myofiber degeneration was less severe in Study B than at the higher doses used in Study A. No degenerative effect on heart muscle was observed in Study B.

The findings of Study B are summarized in Table 4:

TABLE 4

| Dose Regimen | Total Daily Dose (mg/kg) | $C_{max}$ (µg/mL) | $AUC_{0-24 h}$ (µg-h/mL) | Peak CPK (U/L) | Incidence of Microscopic Myopathy[1] |
|---|---|---|---|---|---|
| saline q8h | 0 | 0 | 0 | 150 | 0/28 |
| 5 mg/kg q24h | 5 | 58 | 180 | 150 | 3/28 |
| 5 mg/kg q8h | 15 | 58 | 412 | 500 | 11/28 |

[1]The incidence of microscopic myopathy (last column) shows the number of sites that exhibit minimal degenerative changes divided by the number of sites examined. In this experiment, seven sites were examined in each of four dogs for a total of 28 sites.

At a q24h dosing interval, the NOEL is approximately 5 mg/kg. This NOELq24h results in no CPK changes and only very minimal histopathological evidence of skeletal muscle toxicity. However, these experiments demonstrate that the NOELq24h does not define a threshold plasma concentration for toxicity because administration every 8 hours (i.e., 5 mg/kg q8h) leads to skeletal muscle toxicity evident by increases in CPK and microscopic myopathy even though the $C_{max}$ was similar to that of the 5 mg/kg q24h regimen. Toxicity may be related to time below a given plasma concentration. For example, time below 10 µg/mL is 6 hours at 5 mg/kg q8h compared to 18 hours at 5 mg/kg q24h. See FIG. 1B. These results suggest that the peak plasma concentration of daptomycin associated with no observable skeletal muscle toxicity is dependent upon dosing frequency.

EXAMPLE 3

In order to study the effects of $C_{max}$ of quinupristin/dalfopristin on skeletal muscle toxicity, dogs (4 male dogs/group) are administered dose regimens of saline q8h, quinupristin/dalfopristin 25 mg/kg q24h, quinupristin/dalfopristin 75 mg/kg q24h and quinupristin/dalfopristin 25 mg/kg q8h intravenously for 20 days.

Steady state plasma concentrations of quinupristin/dalfopristin on day 18 of dosing are determined by HPLC. $C_{max}$ levels and AUC are measured as described in Example 1 for 25 mg/kg q8h, 25 mg/kg q24h and 75 mg/kg q24h. Similarly, CPK levels and the incidence of muscle-related histopathological findings are determined as described in Example 1 for 25 mg/kg q8h, 25 mg/kg q24h and 75 mg/kg q24h. For skeletal muscle, six sites are examined in each of four dogs for a total of 24 sites. If no microscopic myopathy or effects on CPK levels are observed at any of the dose regimens, then the doses may be increased. For instance, $C_{max}$ levels and AUC may be measured for 50 mg/kg q8h, 50 mg/kg q24h and 150 mg/kg q24h.

A dosage regimen of 25 mg/kg quinupristin/dalfopristin q8h is expected to result in greater muscle toxicity, as measured by elevated CPK levels and/or a greater incidence of microscopic myopathy, than a dosage regimen of 75 mg/kg quinupristin/dalfopristin q24h. However, $C_{max}$ levels are expected to be higher for 75 mg/kg q24h than $C_{max}$ levels for 25 mg/kg q8h and thus will result in greater efficacy at 75 mg/kg quinupristin/dalfopristin q24h than 25 mg/kg quinupristin/dalfopristin q8h.

EXAMPLE 4

In order to study whether an increased dosing interval would prevent transient skeletal muscle toxicity in patients, daptomycin was administered intravenously to hospitalized adult subjects with serious gram-positive bacteremia or with a variety of infections due to gram-positive bacteria that was resistant to vancomycin or who were otherwise refractory to, or contraindicated for, currently available therapy. The subjects were treated for a period of 7–21 days. Serum CPK levels were determined prior to first antibiotic treatment and every other day for the first seven days of treatment, and daily thereafter.

The results demonstrate that administration of daptomycin to eight patients at a 4 mg/kg dose every 24 hours or to nine patients at a 6 mg/kg dose every 24 hours did not cause an increase in serum CPK levels above the normal range (20–198 U/L) in a majority of patients. See Table 5. Furthermore, even in the few patients who experienced some elevation in CPK levels above normal, the elevation was not considered to be related to daptomycin treatment. None of the patients experienced any muscular pain or weakness and all patients were able to finish the course of daptomycin treatment. Similarly, administration of an initial dose of 6 mg/kg daptomycin followed by 3 mg/kg every 12 hours to three human patients did not cause an increase in CPK levels above normal.

TABLE 5

| Patient | Pre-dose baseline | CPK Range[1] of Observations During Treatment | | Total Number of Patients with Presumed Drug-Related Adverse Skeletal Muscle Effects[2]/ Total Evaluated |
|---|---|---|---|---|
| | | Minimum | Maximum | |
| 6 MG/KG q 24 h | | | | |
| 1 | <18 | <18 | 194 | 0/9 |
| 2 | 129 | 54 | 140 | |
| 3 | NA | <18 | 56 | |
| 4 | 35 | <18 | 43 | |
| 5 | <18 | <18 | <18 | |
| 6 | 44 | <18 | 44 | |
| 7 | 11 | 6 | 101 | |
| 8 | 25 | 8 | 25 | |
| 9 | 284 | 171 | *1324 | |
| 4 MG/KG q 24 h | | | | |
| 1 | 43 | 33 | 59 | 0/8 |
| 2 | 18 | 18 | 35 | |
| 3 | 25 | 19 | 212 | |
| 4 | 44 | <18 | 48 | |
| 5 | 144 | <18 | 144 | |
| 6 | 23 | 20 | 36 | |
| 7 | 37 | 32 | 369** | |
| 8 | <18 | <18 | 26 | |
| 6 MG/KG followed by 3 MG/KG q 12 h | | | | |
| 1 | 78 | 78 | 137 | 0/3 |
| 2 | 29 | <18 | 49 | |
| 3 | <18 | <18 | 34 | |

[1]Normal CPK range 20–192; detectable level 18.
[2]CPK > ULN (192 U/L) and with accompanying clinical signs of pain/weakness or CPK > ULN (192 U/L) without accompanying clinical signs of pain/weakness and with no underlying cause for increased CPK levels.
*Increase in CPK began after 1st dose; returned to baseline while continuing daptomycin treatment. Patient also receiving steroid treatment.
**Value occurred after the 13th dose and returned to baseline with continued treatment.

EXAMPLE 5

Different dosage levels at various dosage intervals of daptomycin are administered to human subjects. Daptomycin is administered intravenously to adult subjects with a diagnosis of an infection due to a gram-positive bacteria strain that is resistant to vancomycin or who are otherwise refractory to, or contraindicated for, currently available therapy. The subjects are treated for a period of 7 to 14 days. The treatment may be extended to 28 to 56 days. Different doses of daptomycin are administered at a dosage interval of once every 24 hours, once every 48 hours, once every 72 hours, once every 96 hours, or once weekly. Other dosage intervals intermediate to or shorter than these dosage intervals may also be used. Dosage levels that may be used include 7, 8, 9, 10, 11, 12, 14, 16, 18, 20, 22 or 25 mg/kg. Other dosage levels that are lower than, intermediate to, or higher than these dosage levels also may be used. The efficacy of the treatment is measured by one or more of the following criteria: eradication or reduction of the gram-positive bacteria blood concentrations that are isolated at admission to the study by microbiological measures; the time in days to microbiological resolution or improvement of the bacterial infection; resolution or improvement of clinical signs and symptoms reported at admission; and survival rates at 3 to 4 weeks after the last dose of antibiotic. A dosage level and interval is efficacious when one or more of the above criteria is satisfied. Serum CPK levels were determined prior to first antibiotic treatment and every other day for the first seven days of treatment, and daily thereafter. A dosage level and interval is safe when it does not cause serum CPK levels to rise significantly above normal levels or when the treatment does not cause skeletal muscular pain or weakness.

EXAMPLE 6

The procedures described in Example 5 are followed essentially as described except that quinupristin/dalfopristin is administered to a patient instead of daptomycin, and the dosage levels range from 7.5 to 30 mg/kg q24h. Dosage levels that may be used include 7.5, 10, 12, 14, 16, 18, 20, 22, 24, 26, 28 or 30 mg/kg. Other dosage levels that are lower than, intermediate to, or higher than these dosage levels also may be used.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for administering daptomycin, comprising the step of administering to a human patient in need thereof a therapeutically effective amount of daptomycin in a dose of 3 to 75 mg/kg of daptomycin at a dosage interval that minimizes skeletal muscle toxicity, wherein the daptomycin dose is repeatedly administered at a dosage interval of once every 24 hours to once every 48 hours.

2. The method according to claim 1, wherein daptomycin is administered at a dosage interval of once every 24 hours or once every 48 hours.

3. The method according to claim 1, wherein the dose is 3 to 12 mg/kg.

4. The method according to claim 3, wherein the dose is 3, 4, 5, 6, 7, 8, 9, 10, 11 or 12 mg/kg.

5. The method according to claim 4, wherein the dose is 4, 6, 8 or 10 mg/kg.

6. The method according to claim 1, wherein the dose is 10 to 25 mg/kg.

7. The method according to claim 6, wherein the dose is 10, 11, 12, 13, 14, 15, 16, 20 or 25 mg/kg.

8. The method according to claim 1, wherein an antibiotic other than daptomycin is co-administered with daptomycin.

9. The method according to claim 8, wherein said antibiotic is selected from the group consisting of penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents, sulfonamides, trimethoprim and its combinations, pyrimethamine, synthetic antibacterials, nitrofuirans, methenamine mandelate, methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone and viomycin.

10. The method according to claim 8, wherein said antibiotic is selected from the group consisting of imipenen, amikacin, netilmicin, fosfomycin, gentamicin and teicoplanin.

11. The method according to claim 8, wherein said administering is via oral, subcutaneous or intravenous administration.

12. A method for administering daptomycin, comprising the step of administering to a human patient in need thereof a therapeutically effective amount of daptomycin at a dose of 3 to 75 mg/kg of daptomycin at a dosage interval that minimizes skeletal muscle toxicity, wherein the daptomycin dose is repeatedly administered at a dosage interval of once every 24 hours.

13. The method according to claim 12, wherein the dose is 3 to 12 mg/kg.

14. The method according to claim 13, wherein the dose is 3, 4, 5, 6, 7, 8, 9, 10, 11 or 12 mg/kg.

15. The method according to claim 14, wherein the dose is 4, 6, 8 or 10 mg/kg.

16. The method according to claim 14, wherein the dose is 4 mg/kg administered once every 24 hours.

17. The method according to claim 14, wherein the dose is 6 mg/kg administered once every 24 hours.

18. The method according to claim 13, wherein the dose is 25 to 75 mg/kg.

19. The method according to claim 18, wherein the dose is 25, 50 or 75 mg/kg.

20. The method according to claim 12, wherein the dose is 10 to 25 mg/kg.

21. The method according to claim 20, wherein the dose is 10, 11, 12, 13, 14, 15, 16, 20 or 25 mg/kg.

22. The method according to either of claims 1 or 12, wherein said administering is via oral, subcutaneous or intravenous administration.

23. The method according to either of claims 1 or 12, wherein the daptomycin is administered for 3 days to 6 months.

24. The method according to either of claims 1 or 12, wherein the daptomycin is administered for 7 to 28 days.

25. The method according to either of claims 1 or 12, wherein the daptomycin is administered for 7 to 14 days.

26. A method for treating or eradicating a bacterial infection in a human patient in need thereof, comprising the step of administering a therapeutically effective amount of daptomycin in a dose of 3 to 75 mg/kg to the patient at a dosage interval that minimizes skeletal muscle toxicity, wherein the daptomycin dose is repeatedly administered at the dosage interval of once every 24 hours to once every 48 hours until said bacterial infection is treated or eradicated.

27. The method according to claim 26, wherein the dose is 3 to 12 mg/kg.

28. The method according to claim 26, wherein the dose is 3, 4, 5, 6, 7, 8, 9, 10, 11 or 12 mg/kg.

29. The method according to claim 26, wherein an antibiotic other than daptomycin is co-administered with daptomycin.

30. The method according to claim 29, wherein said antibiotic is selected from the group consisting of penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents, sulfonamides, trimethoprim and its combinations, pyrimethamine, synthetic antibacterials, nitrofurans, methenamine mandelate, methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone and viomycin.

31. The method according to claim 29, wherein said antibiotic is selected from the group consisting of imipenen, amikacin, netilmicin, fosfomycin, gentamicin and teicoplanin.

32. The method according to any one of claims 26 or 29, wherein said administering is via oral, subcutaneous or intravenous administration.

33. The method according to any one of claims 26 or 29, wherein said administering is once every 24 hours.

34. The method according to claim 33, wherein the dose is 4 mg/kg.

35. The method according to claim 33, wherein the dose is 6 mg/kg.

36. The method according to claim 33, wherein the daptomycin is administered for 3 days to 6 months.

37. The method according to claim 33, wherein the daptomycin is administered for 7 to 28 days.

38. The method according to claim 33, wherein the daptomycin is administered for 7 to 14 days.

39. The method according to either of claims 26 or 29, wherein the daptomycin is administered for 3 days to 6 months.

40. The method according to either of claims 26 or 29, wherein the daptomycin is administered for 7 to 28 days.

41. The method according to either of claims 26 or 29, wherein the daptomycin is administered for 7 to 14 days.

42. The method according to claim 16, wherein said administering is via intravenous administration.

43. The method according to claim 17, wherein said administering is via intravenous administration.

44. The method according to claim 34, wherein said administering is via intravenous administration.

45. The method according to claim 35, wherein said administering is via intravenous administration.

\* \* \* \* \*